US008694112B2

(12) United States Patent
Chapa et al.

(10) Patent No.: US 8,694,112 B2
(45) Date of Patent: Apr. 8, 2014

(54) METHODS AND SYSTEMS FOR FITTING A BILATERAL COCHLEAR IMPLANT PATIENT USING A SINGLE SOUND PROCESSOR

(75) Inventors: Fernando Chapa, Harold, CA (US); Guillermo A. Calle, Moorpark, CA (US); Jacob Johnston, Winnetka, CA (US)

(73) Assignee: Advanced Bionics AG, Zug (CH)

( * ) Notice: Subject to any disclaimer, the term of this patent is extended or adjusted under 35 U.S.C. 154(b) by 910 days.

(21) Appl. No.: 12/847,099

(22) Filed: Jul. 30, 2010

(65) Prior Publication Data

US 2012/0029594 A1 Feb. 2, 2012

Related U.S. Application Data

(63) Continuation of application No. 13/199,836, filed on Sep. 8, 2011.

(51) Int. Cl.
*A61N 1/18* (2006.01)

(52) U.S. Cl.
USPC .......................................................... 607/55

(58) Field of Classification Search
USPC ........................ 607/55–57, 59, 137
See application file for complete search history.

(56) References Cited

U.S. PATENT DOCUMENTS

| 8,352,046 | B1* | 1/2013 | Haller et al. | 607/137 |
| 2004/0208330 | A1 | 10/2004 | Chalupper et al. | |
| 2005/0209657 | A1* | 9/2005 | Chung et al. | 607/57 |
| 2006/0100672 | A1* | 5/2006 | Litvak | 607/57 |
| 2007/0135862 | A1 | 6/2007 | Nicolai et al. | |
| 2010/0070000 | A1* | 3/2010 | Litvak et al. | 607/57 |

FOREIGN PATENT DOCUMENTS

| EP | 0941014 | 2/1999 |
| WO | WO-2009/072040 | 6/2009 |
| WO | WO-2010/076342 | 7/2010 |

OTHER PUBLICATIONS

International Search Report and Written Opinion received in International Application No. PCT/US2011/045674, dated Oct. 26, 2011.

* cited by examiner

*Primary Examiner* — Brian T Gedeon
(74) *Attorney, Agent, or Firm* — ALG Intellectual Property, LLC

(57) ABSTRACT

An exemplary method of fitting a bilateral cochlear implant patient using a single sound processor includes a fitting subsystem using a first sound processor associated with a first cochlear implant to selectively fit the first cochlear implant and a second cochlear implant to a cochlear implant patient, automatically segregating fitting data generated during the fitting of the first cochlear implant from fitting data generated during the fitting of the second cochlear implant, and transmitting the fitting data generated during the fitting of the second cochlear implant to a second sound processor associated with the second cochlear implant after the fitting of the second cochlear implant to the cochlear implant patient is completed. Corresponding methods and systems are also described.

20 Claims, 12 Drawing Sheets

METHODS AND SYSTEMS FOR FITTING A BILATERAL COCHLEAR IMPLANT PATIENT USING A SINGLE SOUND PROCESSOR

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant of a cochlear implant system is initially implanted in a patient, and during follow-up tests and checkups thereafter, it is usually necessary to "fit" the cochlear implant system to the patient. Fitting of a cochlear implant system to a patient is typically performed by an audiologist or the like who presents various stimuli to the patient and relies on subjective feedback from the patient as to how such stimuli are perceived. Adjustments may be made to specifically tailor the parameters of the cochlear implant system to the patient being fitted.

Fitting a cochlear implant system to a patient typically requires multiple pieces of fitting hardware. For example, a clinician's programming interface ("CPI"), its power supply, and various cables are typically required to communicatively couple a fitting station to a sound processor of a cochlear implant system in order to fit the cochlear implant system to a patient. If the patient is a bilateral cochlear implant patient (i.e., has a separate cochlear implant system for each ear), two sets of fitting hardware are typically required. However, some audiologists do not have multiple sets of fitting hardware at their disposal. These audiologists may use a single set of fitting hardware to fit multiple cochlear implants to a bilateral patient. However, currently used techniques to perform such bilateral fitting with a single set of fitting hardware are time-consuming, cumbersome, and difficult for both the audiologist and the patient because of the time required to switch the connection of the single set of fitting hardware from one sound processor to another during a fitting process.

SUMMARY

An exemplary method of fitting a bilateral cochlear implant patient using a single sound processor includes a fitting subsystem using a first sound processor associated with a first cochlear implant to selectively fit the first cochlear implant and a second cochlear implant to a cochlear implant patient, automatically segregating fitting data generated during the fitting of the first cochlear implant from fitting data generated during the fitting of the second cochlear implant, and transmitting the fitting data generated during the fitting of the second cochlear implant to a second sound processor associated with the second cochlear implant after the fitting of the second cochlear implant to the cochlear implant patient is completed.

Another exemplary method of fitting a bilateral cochlear implant patient using a single sound processor includes a fitting subsystem maintaining a first data set associated with a first cochlear implant implanted in a patient and a second data set associated with a second cochlear implant implanted in the patient, using a first sound processor to communicatively couple the fitting subsystem to the first cochlear implant, using the first sound processor to fit the first cochlear implant to the patient in accordance with the first data set while the fitting subsystem is communicatively coupled to the first cochlear implant, using the first sound processor to communicatively couple the fitting subsystem to the second cochlear implant after a communicative decoupling of the fitting subsystem from the first cochlear implant, and using the first sound processor to fit the second cochlear implant to the patient in accordance with the second data set while the fitting subsystem is communicatively coupled to the second cochlear implant.

An exemplary system for fitting a bilateral cochlear implant patient using a single sound processor includes a fitting facility configured to use a first sound processor associated with a first cochlear implant to selectively fit the first cochlear implant and a second cochlear implant to a cochlear implant patient and a data management facility communicatively coupled to the fitting facility and configured to automatically segregate fitting data generated during the fitting of the first cochlear implant from fitting data generated during the fitting of the second cochlear implant and transmit the fitting data generated during the fitting of the second cochlear implant to a second sound processor associated with the second cochlear implant after the fitting of the second cochlear implant is completed.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Methods and systems for fitting a bilateral cochlear implant patient using a single sound processor are described herein. As described in more detail below, a fitting subsystem may be configured to use a first sound processor to selectively fit a first cochlear implant and a second cochlear implant to a bilateral cochlear implant patient. The fitting subsystem may be configured to automatically segregate fitting data associated with the fitting of the first cochlear implant from fitting data associated with the fitting of the second cochlear implant. In some examples, the fitting subsystem may be configured to transfer the fitting data associated with the fitting of the second cochlear implant to a second sound processor associated with the second cochlear implant.

Numerous advantages may be associated with the methods and systems described herein. For example, an audiologist using the fitting subsystem described herein may use a single sound processor to fit first and second cochlear implants to a bilateral cochlear implant patient without having to switch the connection of fitting hardware from one sound processor to another during the fitting process. Accordingly, the audiologist may fit a bilateral cochlear implant without the delay and burden associated with conventional fitting methods and systems that include switching fitting hardware from one sound processor to another.

Figure 1:
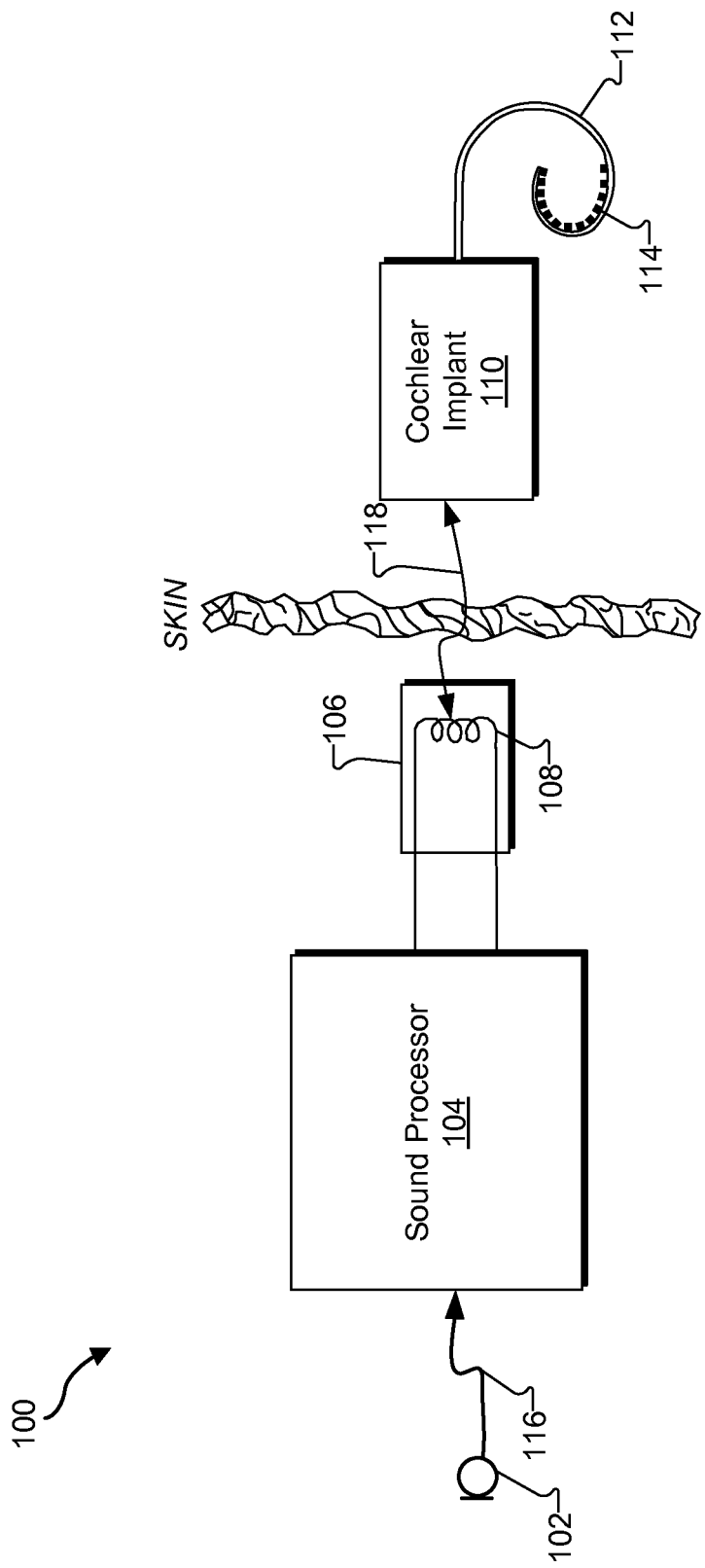
FIG. 1 illustrates an exemplary cochlear implant system according to principles described herein.

To facilitate an understanding of the methods and systems described herein, an exemplary cochlear implant system 100 will be described in connection with FIG. 1. As shown in FIG. 1, cochlear implant system 100 may include a microphone 102, a sound processor 104, a headpiece 106 having a coil 108 disposed therein, a cochlear implant 110 (also referred to as an "implantable cochlear stimulator"), and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct cochlear implant 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling cochlear implant 110. Sound processor 104 may include or be implemented by a behind-the-ear ("BTE") unit, a portable speech processor ("PSP"), and/or any other sound-processing unit as may serve a particular implementation. Exemplary components of sound processor 104 will be described in more detail below.

Sound processor 104 may be configured to transcutaneously transmit, in accordance with a sound processing program associated with cochlear implant 110, one or more control parameters and/or one or more power signals to cochlear implant 110 with coil 108 by way of a communication link 118. These control parameters may be configured to specify one or more stimulation parameters, operating parameters, and/or any other parameter by which cochlear implant 110 is to operate as may serve a particular implementation. Exemplary control parameters include, but are not limited to, stimulation current levels, volume control parameters, program selection parameters, operational state parameters (e.g., parameters that turn a sound processor and/or a cochlear implant on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels ("T levels"), channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within cochlear implant 110. In this manner, control parameters and power signals may be wirelessly transmitted between sound processor 104 and cochlear implant 110 via communication link 118. It will be understood that data communication link 118 may include a bi-directional communication link and/or one or more dedicated uni-directional communication links. In some alternative embodiments, sound processor 104 and cochlear implant 110 may be directly connected with one or more wires or the like.

Cochlear implant 110 may be configured to generate electrical stimulation representative of an audio signal detected by microphone 102 in accordance with one or more stimulation parameters transmitted thereto by sound processor 104. Cochlear implant 110 may be further configured to apply the electrical stimulation to one or more stimulation sites within the cochlea via one or more electrodes 114 disposed along lead 112. In some examples, cochlear implant 110 may include a plurality of independent current sources each associated with a channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by cochlear implant 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

In certain examples, cochlear implant 110, a corresponding data set, and/or a corresponding cochlear implant patient may be associated with a unique identifier (e.g., a unique serial number) stored within cochlear implant 110. The unique identifier may be configured to distinguish cochlear implant 110, a corresponding data set, and/or a corresponding cochlear implant patient from other cochlear implants, data sets, and/or cochlear implant patients. In some examples, the unique identifier may be detectable by sound processor 104 and/or other devices (e.g., by a fitting station) communicatively coupled to cochlear implant 110 and used to identify cochlear implant 110. As will be explained in more detail below, a fitting subsystem may be configured to detect the unique identifier to identify cochlear implant 110 and selectively fit cochlear implant 110 in accordance with a specific data set associated with cochlear implant 110 based on the identification of cochlear implant 110.

As used herein, the term "data set" refers to any data or combination of data associated with a cochlear implant patient and/or the patient's cochlear implant equipment (e.g., a sound processor or cochlear implant). The data set may include identification data (e.g., data identifying a patient, the patient's cochlear implant(s), or the patient's sound processor (s)), measurement data (e.g., data associated with one or more impedance measurements or one or more neural response imaging ("NRI") measurements), visit history data (e.g., data associated with a patient's past visits to an audiologist), control parameter data (e.g., data associated with a set of control parameters selected to optimize a listening experience of the cochlear implant patient), program data (e.g., data associated with one or more sound processing programs), diagnostic data (e.g., data associated with one or more diagnostics procedures), fitting data (e.g., data used or generated during a fitting process including measurement data, control parameter data, diagnostic data, etc.), and/or any other data associated with a cochlear implant patient. An audiologist and/or fitting subsystem may utilize a data set during a fitting process and/or may store additional data within a data set as a result of a fitting process.

Figure 2:
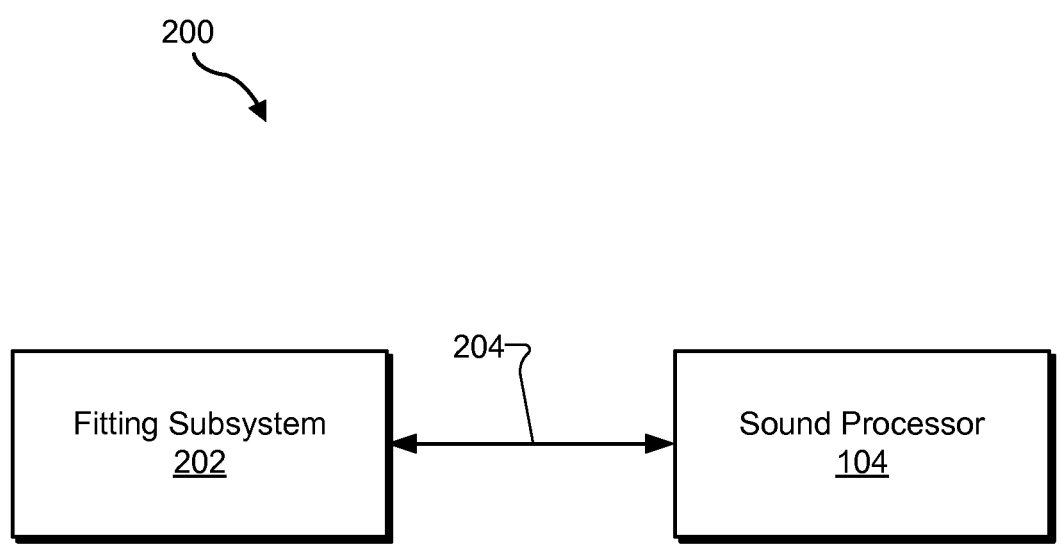
FIG. 2 illustrates an exemplary cochlear implant fitting system according to principles described herein.

FIG. 2 illustrates an exemplary cochlear implant fitting system 200 (or simply "fitting system 200") that may be used to fit sound processor 104 to a patient. As used herein, the terms "fitting a sound processor to a patient" and "fitting a cochlear implant to a patient" will be used interchangeably to refer to performing one or more fitting operations associated with sound processor 104, cochlear implant 110, and/or any other component of cochlear implant system 100. Such fitting operations may include, but are not limited to, adjusting one or more control parameters by which sound processor 104 and/or cochlear implant 110 operate, measuring one or more electrode impedances, performing one or more neural response detection operations, and/or performing one or more diagnostics procedures associated with the cochlear implant system.

As shown in FIG. 2, fitting system 200 may include a fitting subsystem 202 configured to be selectively and communicatively coupled to sound processor 104 of cochlear implant system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. An exemplary implementation of fitting subsystem 202 will be described in more detail below.

Figure 3:
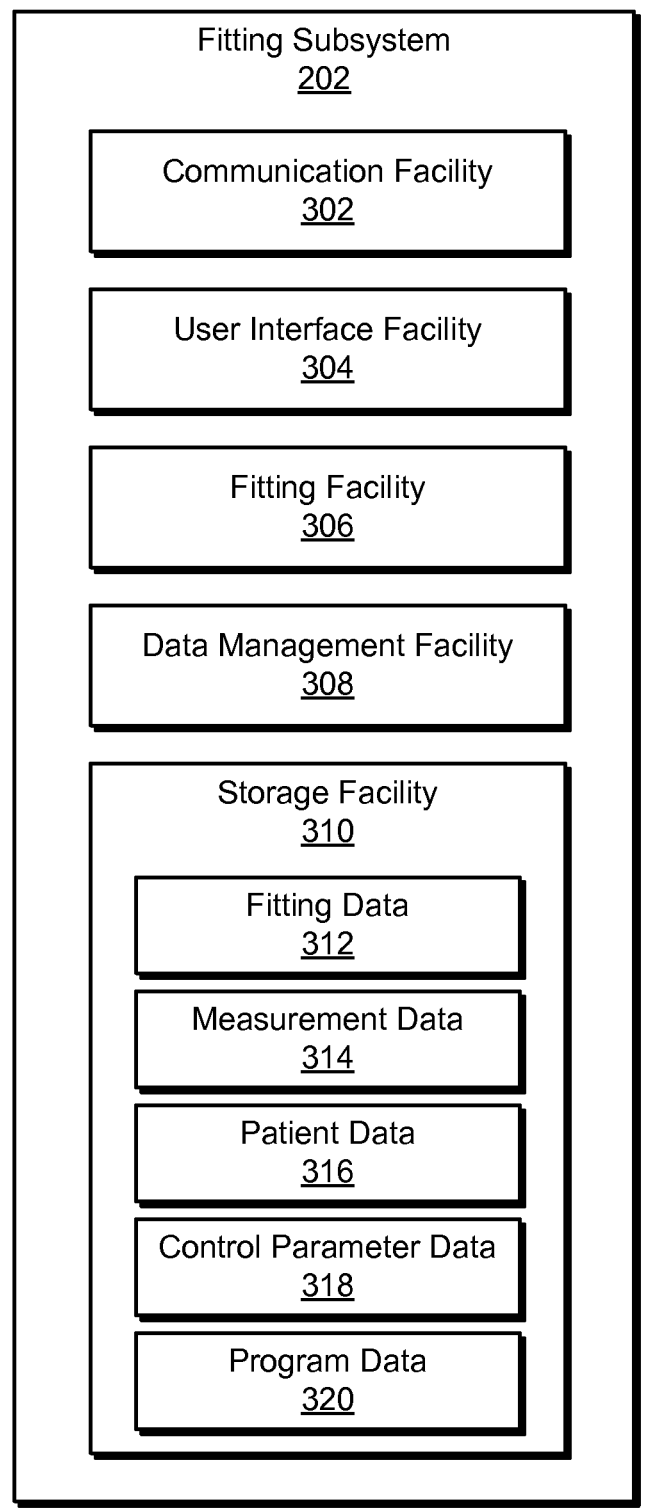
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a user interface facility 304, a fitting facility 306, a data management facility 308, and a storage facility 310, which may be communicatively coupled to one another using any suitable communication technologies. Each of these facilities will now be described in more detail.

Communication facility 302 may be configured to facilitate communication between fitting subsystem 202 and sound processor 104. For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

Communication facility 302 may be configured to selectively communicate with a first cochlear implant and a second cochlear implant by way of sound processor 104 during a fitting process. For example, communication facility 302 may be configured to communicate with the first cochlear implant (e.g., direct sound processor 104 to transmit/receive signals to/from the first cochlear implant) when sound processor 104 is communicatively coupled to the first cochlear implant and communicate with the second cochlear implant (e.g., direct sound processor 104 to transmit/receive signals to/from the second cochlear implant) when sound processor 104 is communicatively coupled to the second cochlear implant. In some examples, communication facility 302 may be configured to detect a communicative coupling by sound processor 104 to either the first cochlear implant or the second cochlear implant. For example, communication facility 302 may be configured to detect a first unique identifier associated with the first cochlear implant and detect a second unique identifier associated with the second cochlear implant by way of sound processor 104.

Communication facility 302 may additionally or alternatively be configured to facilitate communication between fitting subsystem 302 and one or more other devices. For example, communication facility 302 may be configured to facilitate communication between fitting subsystem 302 and one or more computing devices (e.g., by way of the Internet and/or one or more other types of networks), reference implants, and/or any other computing device as may serve a particular implementation.

User interface facility 304 may be configured to provide one or more user interfaces configured to facilitate user interaction with fitting subsystem 202. For example, user interface facility 304 may provide a graphical user interface ("GUI") through which one or more functions, options, features, and/or tools associated with one or more fitting operations described herein may be provided to a user and through which user input may be received. In certain embodiments, user interface facility 304 may be configured to provide the GUI to a display device (e.g., a computer monitor) for display. In some examples, user interface facility 304 may be configured to provide a first graphical user interface configured to facilitate interaction by a user with a first cochlear implant and a second graphical user interface configured to facilitate interaction by the user with a second cochlear implant, as will be explained in more detail below.

Fitting facility 306 may be configured to perform one or more of the fitting operations described herein. For example, fitting facility 306 may be configured to adjust one or more control parameters by which sound processor 104 and/or cochlear implant 110 operate, direct sound processor 104 to measure one or more electrode impedances, perform one or more neural response detection operations, and/or perform one or more diagnostics procedures associated with cochlear implant system 100.

Fitting facility 306 may additionally or alternatively be configured to use a single sound processor (e.g., sound processor 104) to selectively fit a first cochlear implant and a second cochlear implant to a cochlear implant patient. For example, fitting facility 306 may be configured to use sound processor 104 to perform one or more fitting operations associated with the first cochlear implant when sound processor 104 is communicatively coupled to the first cochlear implant and use sound processor 104 to perform one or more fitting operations associated with the second cochlear implant when sound processor 104 is communicatively coupled to the second cochlear implant, as will be explained in more detail below.

In some examples, fitting facility 306 may be configured to initialize sound processor 104 prior to using sound processor 104 to fit one or more cochlear implants to a patient. Such initialization may include, but is not limited to, associating sound processor 104 with a particular patient (e.g., associating sound processor 104 with patient-specific fitting data), associating sound processor 104 with a particular cochlear implant 110, loading data onto sound processor 104, clearing data from sound processor 104, and/or otherwise preparing sound processor 104 for a fitting session in which sound processor 104 is to be fitted to a patient.

Data management facility 308 may be configured to automatically segregate data associated with a first cochlear implant from data associated with a second cochlear implant. For example, data management facility 308 may be configured to automatically segregate fitting data generated during a fitting of the first cochlear implant to a patient from fitting data generated during a fitting of the second cochlear implant to the patient.

Once the fitting of a first cochlear implant and a second cochlear implant using a single sound processor is complete, data management facility 308 may be configured to transfer fitting data generated during the fitting of the second cochlear implant to another sound processor. Accordingly, an audiologist can use a first sound processor (e.g., a sound processor associated with the first cochlear implant) to fit both the first and second cochlear implants to the patient and then transfer fitting data generated during the fitting of the second cochlear implant to a second sound processor (e.g., a sound processor associated with the second cochlear implant) for use by the second sound processor thereafter (e.g., allowing the second sound processor to operate in accordance with any changes made during the fitting process).

Data management facility 308 may additionally or alternatively be configured to maintain one or more data sets associated with one or more cochlear implants, sound processors, and/or patients. For example, data management facility 308 may be configured to maintain a first data set associated with a first cochlear implant of a bilateral cochlear implant patient and a second data set associated with a second cochlear implant of the bilateral cochlear implant patient. The first and second data sets may include any data related to the first and second cochlear implants, respectively, of the bilateral cochlear implant patient, including any data disclosed herein. In some examples, data management facility 308 may be configured to dynamically use, modify, and/or store data in the first and second data sets, as will be described in more detail below.

Storage facility 310 may be configured to maintain fitting data 312 associated with one or more fitting operations, measurement data 314 representative of one or more measurements, patient data 316 representative of data descriptive of or otherwise associated with one or more cochlear implant patients, control parameter data 318 representative of one or more control parameters, and program data 320 representative of one or more sound processing programs, any or all of which may be maintained within one or more data sets. Storage facility 310 may be configured to maintain additional or alternative data as may serve a particular implementation.

Figure 4:
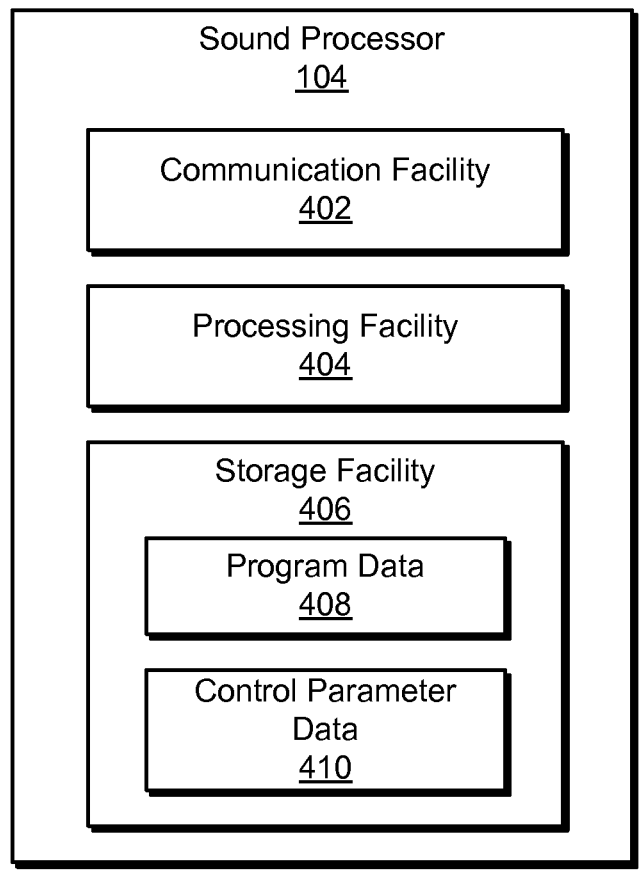
FIG. 4 illustrates exemplary components of an exemplary sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and cochlear implant 110. For example, communication facility 402 may include transceiver components configured to wirelessly transmit data (e.g., control parameters and/or power signals) to cochlear implant 110 and/or wirelessly receive data from cochlear implant 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of cochlear implant 110 (e.g., one or more stimulation parameters defining the electrical stimulation to be generated and applied by cochlear implant 110). In some examples, processing facility 404 may be configured to operate in accordance with one or more sound processing programs provided by fitting subsystem 202 and/or otherwise stored within storage facility 406.

Storage facility 406 may be configured to maintain program data 408 representative of one or more sound processing programs and control parameter data 410 representative of one or more control parameters. Storage facility 406 may be configured to maintain additional or alternative data as may serve a particular implementation.

Figure 5:
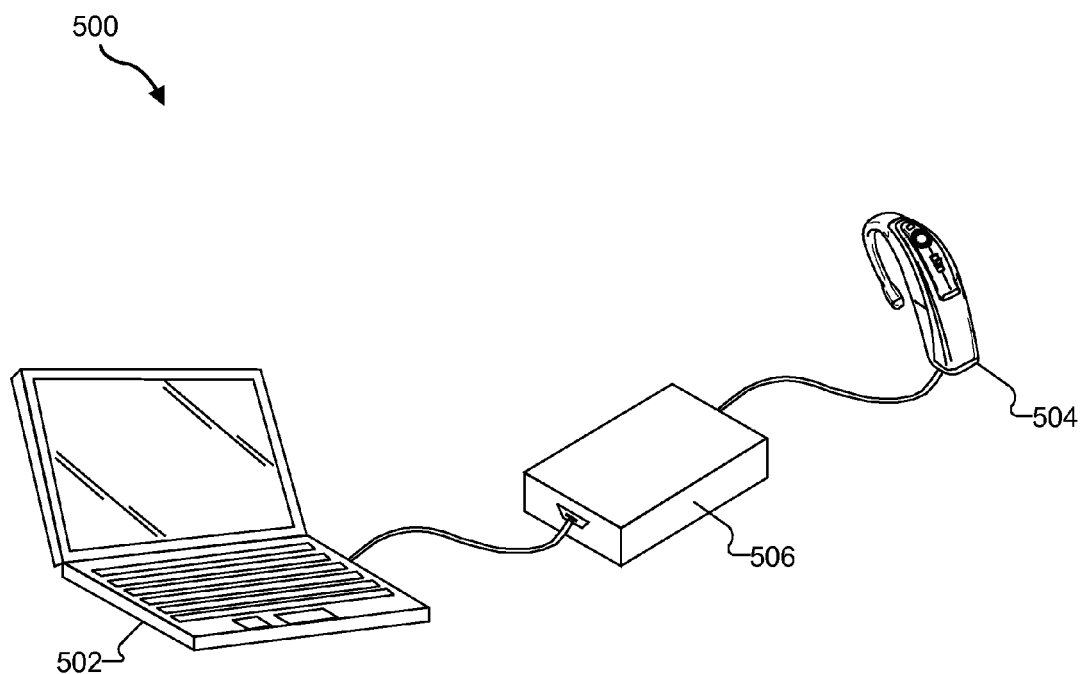
FIG. 5 illustrates an exemplary implementation of the cochlear implant fitting system of FIG. 2 according to principles described herein.

FIG. 5 illustrates an exemplary implementation 500 of fitting system 200. In implementation 500, a fitting station 502 may be selectively and communicatively coupled to a BTE unit 504 by way of a CPI device 506. BTE unit 504 is merely exemplary of the many different types of sound processors that may be used in accordance with the systems and methods described herein. Fitting station 502 may be selectively and communicatively coupled to any other type of sound processor as may serve a particular implementation.

Fitting station 502 may include any suitable computing device and/or combination of computing devices and be configured to perform one or more of the fitting operations described herein. For example, fitting station 502 may display one or more GUIs configured to facilitate selection of one or more measurements to perform using BTE unit 504, selection of one or more sound processing programs by which BTE unit 504 operates, adjustment of one or more control parameters by which BTE unit 504 operates, and/or any other fitting operation as may serve a particular implementation. Fitting station 502 may be utilized by an audiologist, a clinician, and/or any other user to fit one or more cochlear implants to a patient using BTE unit 504.

BTE unit 504 may be configured to selectively and communicatively couple to one or more cochlear implants. In this manner, BTE unit 504 may be configured to facilitate the fitting of the one or more cochlear implants by fitting station 502.

CPI device 506 may be configured to facilitate communication between fitting station 502 and BTE unit 504. In some examples, CPI device 506 may be selectively and communicatively coupled to fitting station 502 and/or BTE unit 504 by way of one or more ports included within fitting station 502 and BTE unit 504.

Figure 6:
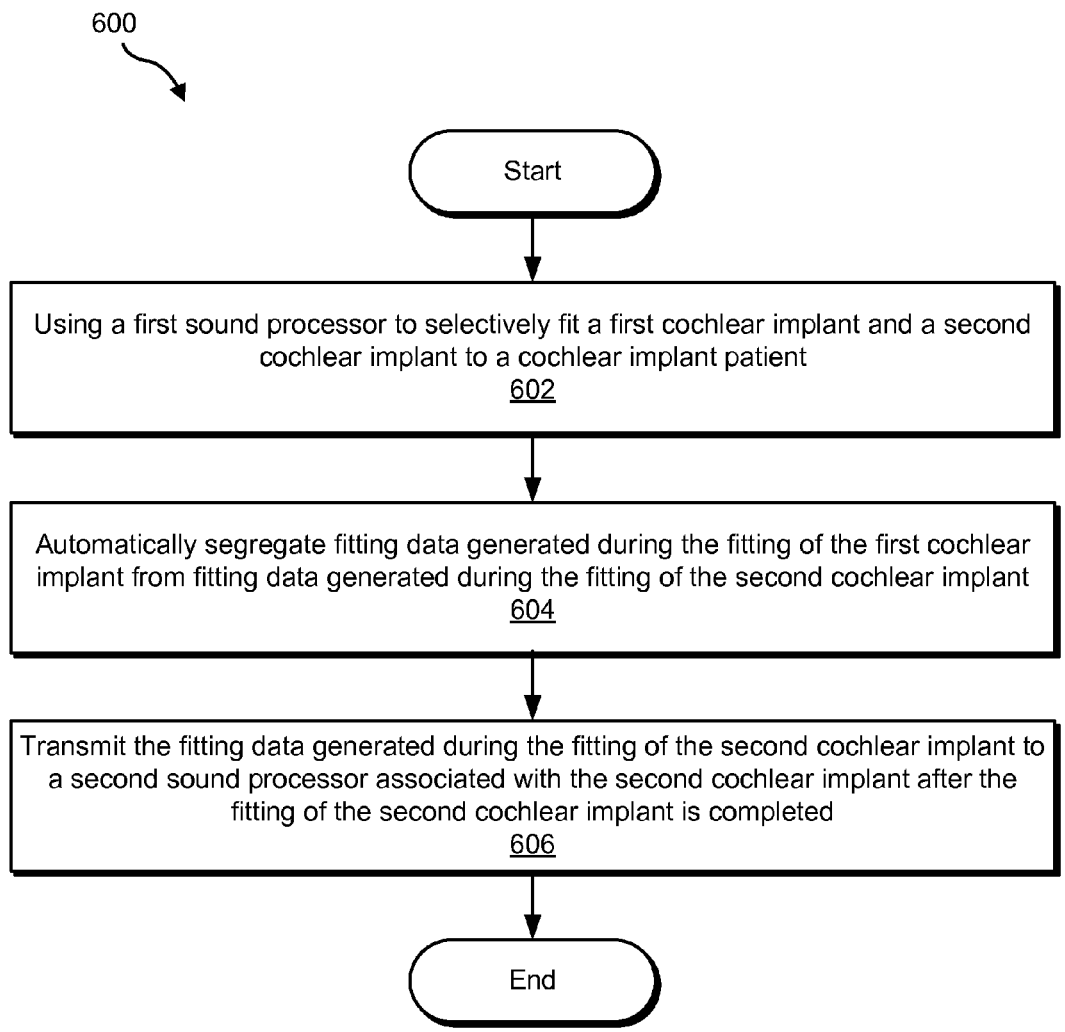
FIG. 6 illustrates an exemplary method of fitting a bilateral cochlear implant patient using a single sound processor according to principles described herein.

FIG. 6 illustrates an exemplary method 600 of fitting a bilateral cochlear implant patient using a single sound processor. While FIG. 6 illustrates exemplary steps according to one embodiment, other embodiments may omit, add to, reorder, and/or modify any of the steps shown in FIG. 6. One or more of the steps shown in FIG. 6 may be performed by any component or combination of components of fitting subsystem 202 and/or fitting station 502.

In step 602, a first sound processor is used to selectively fit a first cochlear implant and a second cochlear implant to a cochlear implant patient. For example, as described above, fitting subsystem 202 may be configured to use sound processor 104 to selectively fit a first cochlear implant and a second cochlear implant to a bilateral cochlear implant patient.

Figure 7:
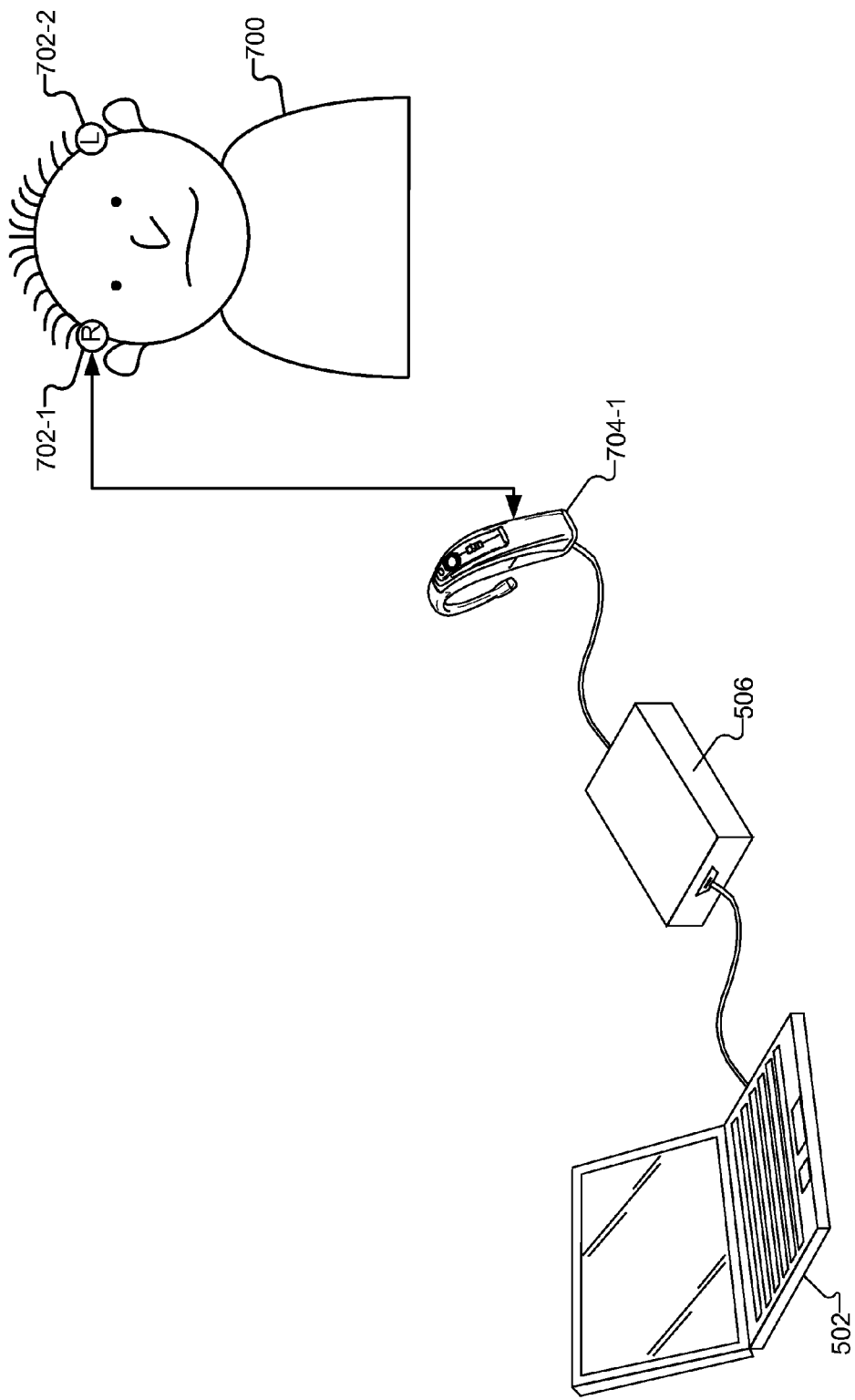
FIG. 7 illustrates an exemplary fitting of a first cochlear implant to a bilateral cochlear implant patient using a first sound processor according to principles described herein.
Figure 8:
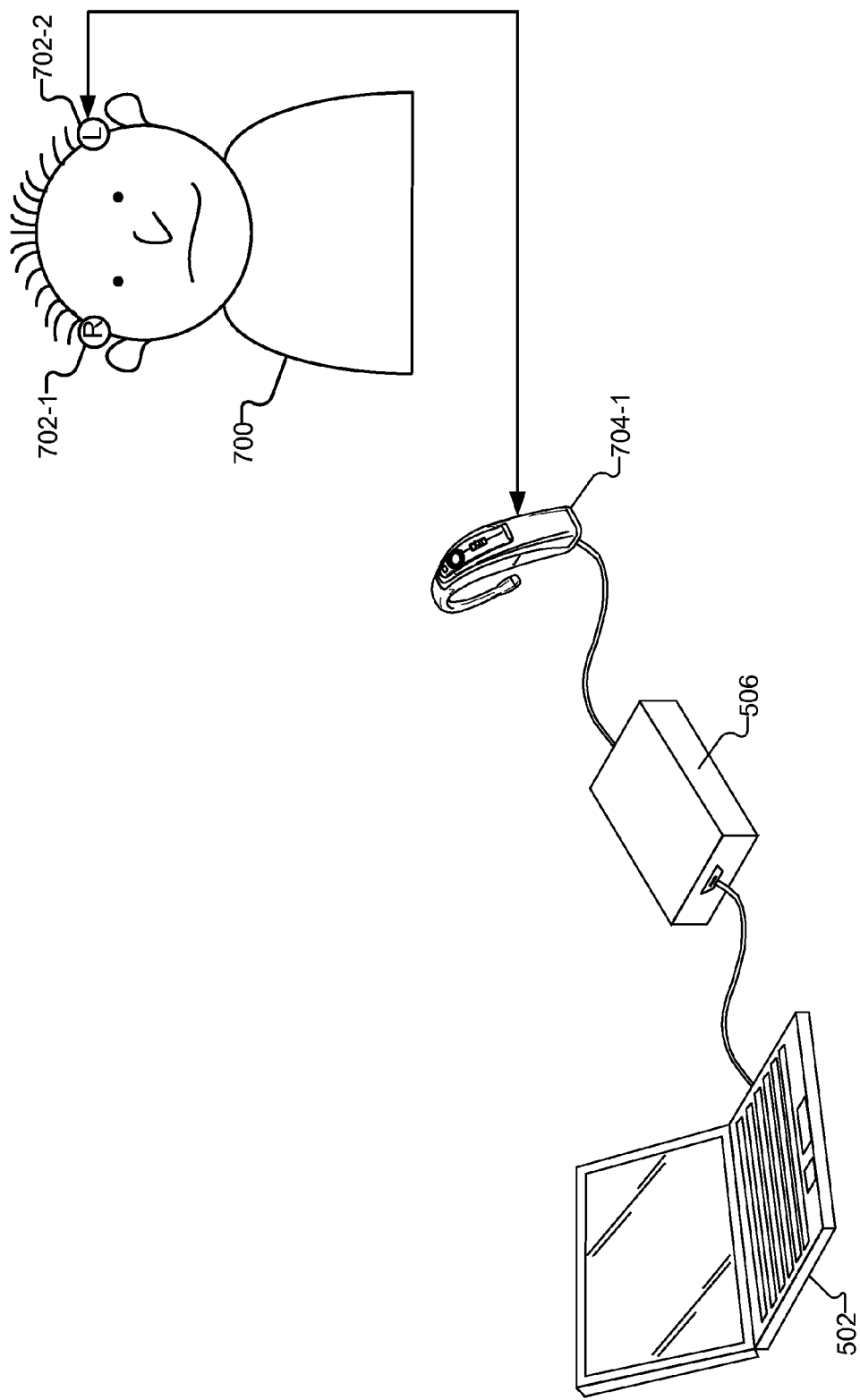
FIG. 8 illustrates an exemplary fitting of a second cochlear implant to the bilateral cochlear implant patient of FIG. 7 using the first sound processor of FIG. 7 according to principles described herein.

FIGS. 7-8 illustrate an exemplary selective fitting of a first cochlear implant and a second cochlear implant to a cochlear implant patient using a single sound processor. FIG. 7 illustrates a bilateral cochlear implant patient 700 (or simply "patient 700") having a first cochlear implant 702-1 and a second cochlear implant 702-2 (referred to collectively herein as "a cochlear implants 702"). First cochlear implant 702-1 may be implanted in patient 700 and associated with a first ear (e.g., the right ear) of patient 700 and second cochlear implant 702-2 may be implanted in patient 700 and associated with a second ear (e.g., the left ear) of patient 700.

As shown, an audiologist may use fitting station 502, CPI 506, and a first sound processor 704-1 to fit first cochlear implant 702-1 to patient 700. In some examples, first sound processor 704-1 may be associated with first cochlear implant 702-1. In other words, first sound processor 704-1 is configured to be normally paired with first cochlear implant 702-1 in a non-fitting environment.

To facilitate the fitting of first cochlear implant 702-1, fitting station 502 may use CPI 506 and first sound processor 704-1 to communicatively couple fitting station 502 to first cochlear implant 702-1. For example, the audiologist may connect first sound processor 704-1 to CPI 506 and then the audiologist or patient 700 may facilitate the communicative coupling of first sound processor 704-1 to the first cochlear implant 702-1 (e.g., by placing first sound processor 704-1 behind the patient's right ear and positioning a corresponding headpiece to communicate with first cochlear implant 702-1).

In some examples, fitting station 502 may be configured to detect when fitting station 502 is communicatively coupled to first cochlear implant 702-1. For example, fitting station 502 may be configured to detect a transmission of one or more signals between first sound processor 704-1 and first cochlear implant 702-1. Additionally or alternatively, fitting station 502 may be configured to uniquely identify first cochlear implant 702-1. For example, fitting station 502 may be configured to detect a first unique serial number associated with and stored by first cochlear implant 702-1 and identify first cochlear implant 702-1 based on the first unique serial number. In some examples, fitting station 502 may be configured to dynamically operate in response to the detection and/or identification of first cochlear implant 702-1, as will be explained in more detail below.

While fitting station 502 is communicatively coupled to first cochlear implant 702-1 by way of first sound processor 704-1, fitting station 502 may use first sound processor 704-1 to fit first cochlear implant 702-1 to patient 700. For example, an audiologist may use fitting station 502 and/or first sound processor 704-1 to adjust one or more control parameters by which first cochlear implant 702-1 operates, measure one or more electrode impedances associated with first cochlear implant 702-1, perform one or more neural response detection operations associated with first cochlear implant 702-1, and/or perform one or more diagnostics procedures associated with first cochlear implant 702-1.

In some examples, fitting station 502 may be configured to fit first cochlear implant 702-1 to patient 700 in accordance with a first data set associated with first cochlear implant 702-1. For example, in response to a detection of the communicative coupling of fitting station 502 to first cochlear implant 702-1, fitting station 502 may be configured to access the first data set and dynamically use, modify, and/or store data within the first data set during the fitting of first cochlear implant 702-1. The first data set may include any suitable fitting data, measurement data, patient data, and/or any other applicable data, such as disclosed herein. In some examples, the first data set may be associated with the first unique serial number of the first cochlear implant 702-1. As a result, upon a detection of the first unique serial number by fitting station 502, fitting station 502 may use the first unique serial number to identify and access the first data set and then fit first cochlear implant 702-1 in accordance with the first data set.

Once the one or more fitting operations associated with first cochlear implant 702-1 are completed, the audiologist may use fitting station 502, CPI 506, and first sound processor 704-1 to fit second cochlear implant 702-2 to patient 700.

For example, as shown in FIG. 8, the audiologist may switch first sound processor 704-1 from being coupled to first cochlear implant 702-1 to being coupled to second cochlear implant 702-2 to establish a communicative coupling of fitting station 502 to second cochlear implant 702-2 by way of first sound processor 704-1. In some examples, fitting station 502 may be configured to detect the communicative decoupling of first sound processor 704-1 from first cochlear implant 702-1 and detect the subsequent coupling of first sound processor 704-1 to second cochlear implant 702-2. In some examples, fitting station 502 may be configured to detect a second unique serial number associated with and stored by second cochlear implant 702-2 and identify second cochlear implant 702-2 based on the second unique serial number. Additionally or alternatively, fitting station 502 may be configured to dynamically operate in response to the detection and/or identification of second cochlear implant 702-2, as will be explained in more detail below.

While fitting station 502 is communicatively coupled to second cochlear implant 702-2 by way of first sound processor 704-1, fitting station 502 may use first sound processor 704-1 to fit second cochlear implant 702-2 to patient 700. For example, an audiologist may use fitting station 502 and/or first sound processor 704-1 to adjust one or more control parameters by which second cochlear implant 702-2 operates, measure one or more electrode impedances associated with second cochlear implant 702-2, perform one or more neural response detection operations associated with second cochlear implant 702-2, and/or perform one or more diagnostics procedures associated with second cochlear implant 702-2.

In some examples, fitting station 502 may be configured to fit second cochlear implant 702-2 to patient 700 in accordance with a second data set associated with second cochlear implant 702-2. For example, in response to a detection and/or identification of second cochlear implant 702-2, fitting station 502 may be configured to access the second data set and dynamically use, modify, and/or store data within the second data set during the fitting of second cochlear implant 702-2. In some examples, the second data set may be associated with the second unique serial number of the second cochlear implant 702-2. As a result, upon a detection of the second unique serial number by fitting station 502, fitting station 502 may use the second unique serial number to identify and access the second data set and then fit second cochlear implant 702-2 in accordance with the second data set.

Once the one or more fitting operations associated with second cochlear implant 702-2 are completed, the audiologist may desire to perform one or more additional fitting operations associated with first cochlear implant 702-1 and thereafter perform one or more additional fitting operations associated with second cochlear implant 702-2, and so on. Fitting station 502 may be configured to dynamically adapt to any number of switches of first sound processor 704-1 between first cochlear implant 702-1 and second cochlear implant 702-2 in a manner similar to that described above.

Figure 9:
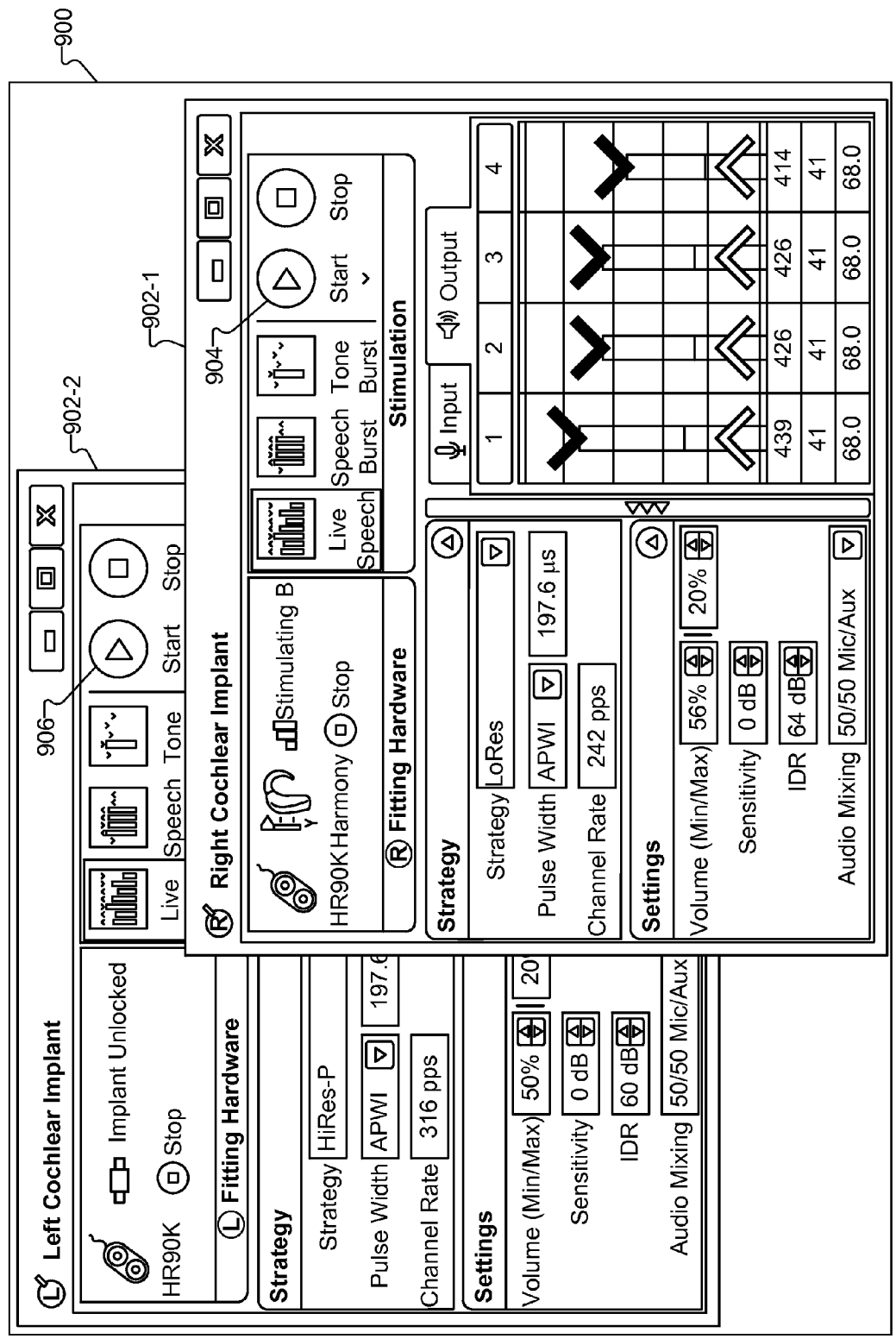
FIG. 9 shows exemplary graphical user interfaces ("GUIs") that may be presented for display according to principles described herein.

Fitting station 502 may additionally or alternatively be configured to provide one or more graphical user interfaces ("GUIs") for display to an audiologist to facilitate interaction with cochlear implants 702. For example, as shown in FIG. 9, fitting station 502 may be configured to provide a display 900 of a first GUI 902-1 configured to facilitate interaction by a user with first cochlear implant 702-1 (e.g., to facilitate interaction by the user with first cochlear implant 702-1 when first sound processor 704-1 is communicatively coupled or "locked" to first cochlear implant 702-1) and a second GUI 902-2 configured to facilitate interaction by the user with second cochlear implant 702-2 (e.g., to facilitate interaction by the user with second cochlear implant 702-2 when first sound processor 704-1 is communicatively coupled or "locked" to second cochlear implant 702-2). It will be recognized that GUIs 902-1 and 902-2 are merely illustrative of the many different GUIs that may be presented for display by fitting station 502.

A user may use first GUI 902-1 to access information associated with first cochlear implant 702-1 (e.g., access a first data set associated with first cochlear implant 702-1), adjust one or more control parameters associated with first cochlear implant 702-1, and/or selectively start, stop, and/or resume execution of a fitting operation associated with first cochlear implant 702-1. For example, the user may use first GUI 902-1 to provide user input representative of one or more control parameter values and a particular sound processing program to be used by first cochlear implant 702-1 and select a "start option" 904 to direct first cochlear implant 702-1 to begin a fitting operation in accordance with the selected control parameter values and sound processing program.

Similarly, a user of fitting station 502 may use second GUI 902-2 to access information associated with second cochlear implant 702-2 (e.g., access a second data set associated with second cochlear implant 702-2), adjust one or more control parameters associated with second cochlear implant 702-2, and/or selectively start, stop, and/or resume execution of a fitting operation associated with second cochlear implant 702-2. For example, the user may use second GUI 902-2 to provide user input representative of one or more control parameter values and a particular sound processing program to be used by second cochlear implant 702-2 and select a "start option" 906 to direct second cochlear implant 702-2 to begin a fitting operating in accordance with the selected control parameter values and sound processing program.

A user of fitting station 502 may switch between GUIs 902-1 and 902-2 to selectively fit first cochlear implant 702-1 and second cochlear implant 702-2 to patient 700. In some examples, fitting station 502 may be configured to automatically enable first GUI 902-1 and disable second GUI 902-2 in response to a detection that fitting station 502 is communicatively coupled with first cochlear implant 702-1. Similarly, fitting station 502 may be configured to automatically enable second GUI 902-2 and disable first GUI 902-1 in response to a detection that fitting station 502 is communicatively coupled with second cochlear implant 702-2. In this manner, fitting station 502 may facilitate dynamic and rapid switching between the fitting of first cochlear implant 702-1 and the fitting of second cochlear implant 702-2 while preventing inadvertent modification by a user of the fitting data associated with one of the cochlear implants (e.g., first cochlear implant 702-1) while the other cochlear implant (e.g., cochlear implant 702-2) is communicatively coupled to fitting station 502.

Returning to FIG. 6, in step 604, fitting data generated during the fitting of the first cochlear implant is automatically segregated from fitting data generated during the fitting of the second cochlear implant. For example, data management facility 308 may be configured to automatically segregate fitting data generated during the fitting of the first cochlear implant from the fitting data generated during the fitting of the second cochlear implant in any suitable manner. In some examples, data management facility 308 may be configured to automatically store the fitting data generated during the fitting of the first cochlear implant in a first data set associated with the first cochlear implant and automatically store the fitting data generated during the fitting of the second cochlear implant in a second data set associated with the second cochlear implant. Accordingly, data management facility 308 may be configured to dynamically adapt and automatically manage data in accordance with changes during the fitting process between the first cochlear implant and the second cochlear implant.

The automatic segregation of the fitting data may be based on a detection of a communicative coupling to either the first or the second cochlear implant. For example, data management facility 308 may be configured to automatically segregate fitting data generated while fitting subsystem 202 is communicatively coupled to the first cochlear implant from fitting data generated while fitting subsystem 202 is communicatively coupled to the second cochlear implant. Additionally or alternatively, data management facility 308 may be configured to associate fitting data generated during the fitting of a first cochlear implant with a first unique serial number associated with the first cochlear implant and associate fitting data generated during the fitting of a second cochlear implant with a second unique serial number associated with the second cochlear implant.

In step 606, the fitting data generated during the fitting of the second cochlear implant is transmitted to a second sound processor associated with the second cochlear implant after the fitting of the second cochlear implant is completed. To this end, the first sound processor may be communicatively decoupled from the fitting subsystem and the second sound processor may be communicatively coupled to the fitting subsystem.

Figure 10:
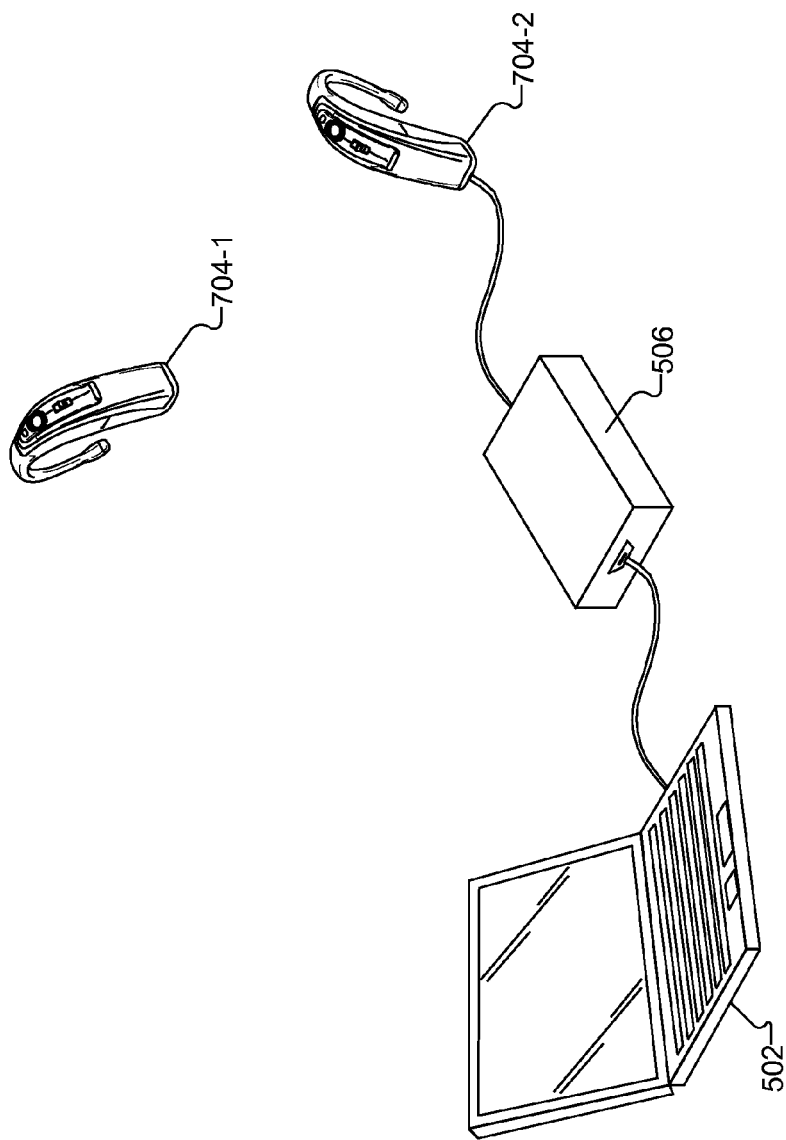
FIG. 10 illustrates an exemplary coupling of a second sound processor to a fitting station and clinician's programming interface ("CPI") according to principles described herein.

For example, FIG. 10 illustrates that after the fitting process is complete, an audiologist may disconnect fitting station 502 and CPI 506 from first sound processor 704-1 and subsequently connect fitting station 502 and CPI 506 to a second sound processor 704-2 associated with second cochlear implant 702-2. After establishing the connection with second sound processor 704-2, fitting station 502 may transmit fitting data generated during the fitting of second cochlear implant 702-2 to second sound processor 704-2. The transmission of the fitting data may be performed in response to input from an audiologist or in response to a detection of the communicative coupling of fitting station 502 with second sound processor 704-2. Once the transmission is complete, second sound processor 704-2 may thereafter operate in accordance with the fitting data generated during the fitting of second cochlear implant 702-2, despite the fact that second sound processor 704-2 was not used to fit second cochlear implant 702-2 to patient 700.

Figure 11:
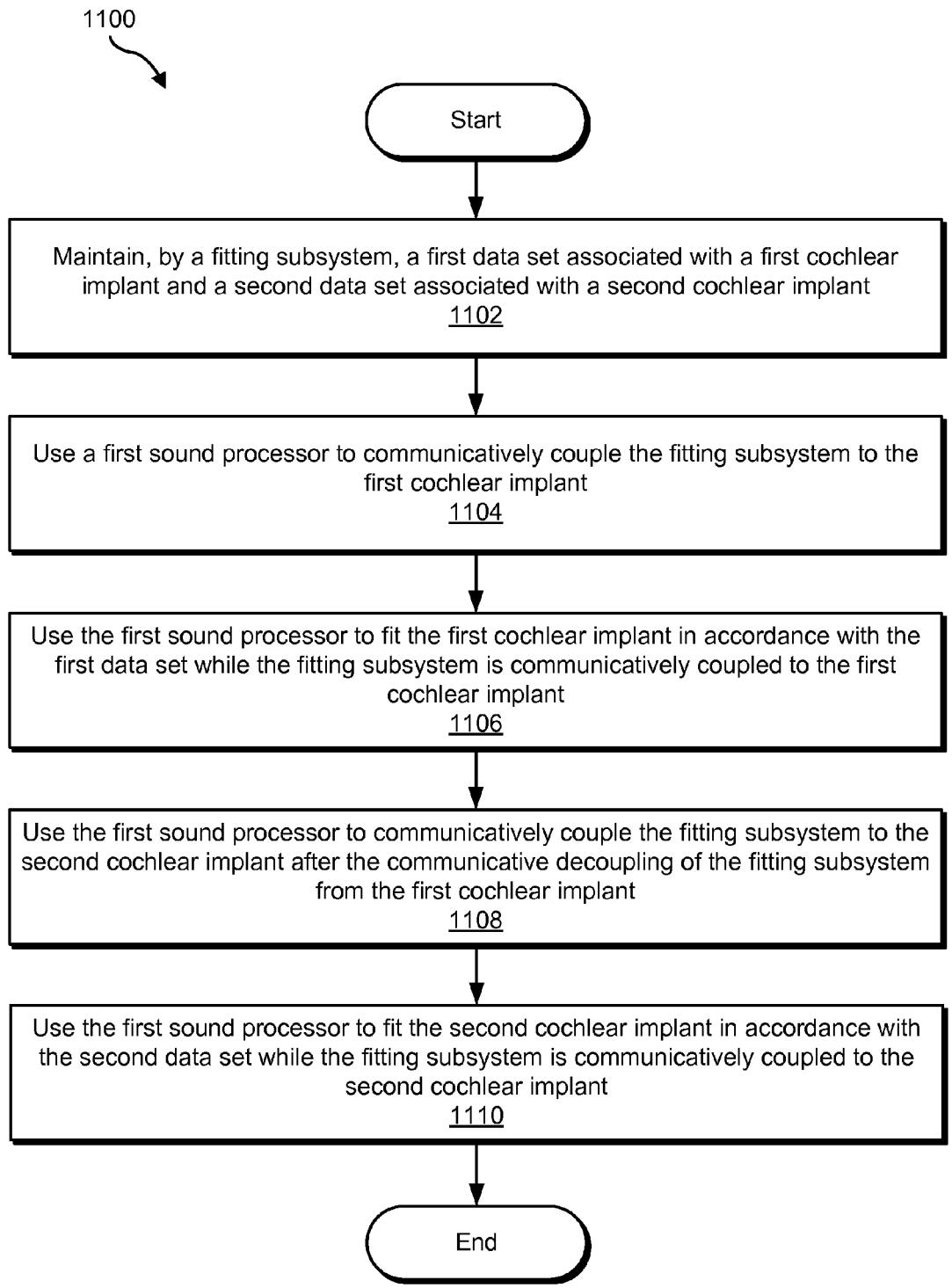
FIG. 11 illustrates another exemplary method of fitting a bilateral cochlear implant patient using a single sound processor according to principles described herein.

FIG. 11 illustrates another exemplary method 1100 of fitting multiple cochlear implants to a bilateral cochlear implant patient using a single sound processor. While FIG. 11 illustrates exemplary steps according to one embodiment, other embodiments may omit, add to, reorder, and/or modify any of the steps shown in FIG. 11. One or more of the steps shown in FIG. 11 may be performed by any component or combination of components of fitting subsystem 202 and/or fitting station 502.

In step 1102, a fitting subsystem maintains a first data set associated with a first cochlear implant and a second data set associated with a second cochlear implant. Step 1102 may be performed in any of the ways described herein.

In step 1104, a first sound processor is used by the fitting subsystem to communicatively couple the fitting subsystem to the first cochlear implant. Step 1104 may be performed in any of the ways described herein.

In step 1106, the first sound processor is used to fit the first cochlear implant in accordance with the first data set while the fitting subsystem is communicatively coupled to the first cochlear implant. Step 1106 may be performed in any of the ways described herein.

In step 1108, the first sound processor is used to communicatively couple the fitting subsystem to the second cochlear implant after a communicative decoupling of the fitting subsystem from the first cochlear implant. Step 1108 may be performed in any of the ways described herein.

In step 1110, the first sound processor is used to fit the second cochlear implant in accordance with the second data set while the fitting subsystem is communicatively coupled to the second cochlear implant. Step 1110 may be performed in any of the ways described herein.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 12:
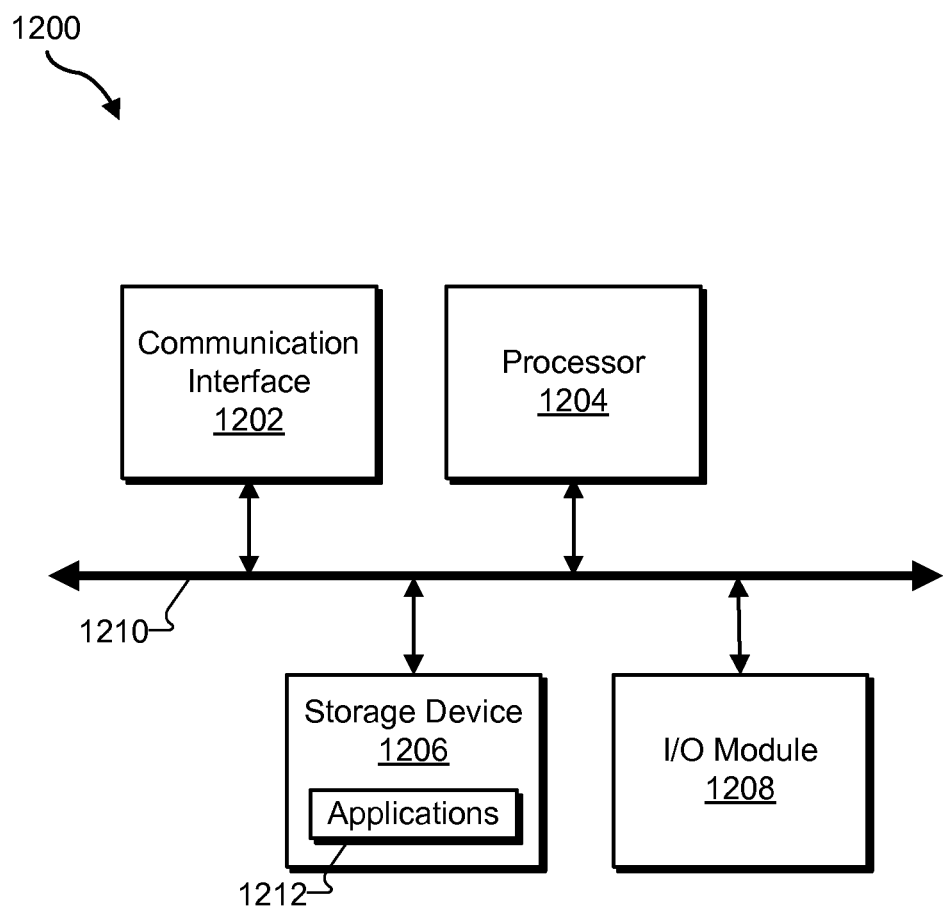
FIG. 12 illustrates an exemplary computing device according to principles described herein.

FIG. 12 illustrates an exemplary computing device 1200 that may be configured to perform one or more of the processes described herein. As shown in FIG. 12, computing device 1200 may include a communication interface 1202, a processor 1204, a storage device 1206, and an input/output ("I/O") module 1208 communicatively connected via a communication infrastructure 1210. While an exemplary computing device 1200 is shown in FIG. 12, the components illustrated in FIG. 12 are not intended to be limiting. Additional or alternative components may be used in other embodiments.

Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, and any other suitable interface. Communication interface 1202 may additionally or alternatively provide such a connection through, for example, a local area network (such as an Ethernet network), a personal area network, a telephone or cable network, a satellite data connection, a dedicated URL, or any other suitable connection. Communication interface 1202 may be configured to interface with any suitable communication media, protocols, and formats, including any of those mentioned above.

Processor 1204 generally represents any type or form of processing unit capable of processing data or interpreting, executing, and/or directing execution of one or more of the instructions, processes, and/or operations described herein. Processor 1204 may direct execution of operations in accordance with one or more applications 1212 or other computer-executable instructions such as may be stored in storage device 1206 or another non-transitory computer-readable medium.

Storage device 1206 may include one or more data storage media, devices, or configurations and may employ any type, form, and combination of data storage media and/or device. For example, storage device 1206 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1206. For example, data representative of one or more executable applications 1212 (which may include, but are not limited to, one or more of the software applications described herein) configured to direct processor 1204 to perform any of the operations described herein may be stored within storage device 1206. In some examples, data may be arranged in one or more databases residing within storage device 1206.

I/O module 1208 may be configured to receive user input and provide user output and may include any hardware, firmware, software, or combination thereof supportive of input and output capabilities. For example, I/O module 1208 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1208 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1200. For example, one or more applications 1212 residing within storage device 1206 may be configured to direct processor 1204 to perform one or more processes or functions associated with communication facility 302, user interface facility 304, fitting facility 306, data management facility 308, communication facility 402, and/or processing facility 404. Likewise, storage facility 310 and/or storage facility 406 may be implemented by or within storage device 1206.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
   using, by a fitting subsystem, a first sound processor separate from the fitting subsystem to selectively fit a first cochlear implant and a second cochlear implant to a cochlear implant patient, wherein the first sound processor is associated with the first cochlear implant;
   automatically segregating, by the fitting subsystem, fitting data generated during the fitting of the first cochlear implant from fitting data generated during the fitting of the second cochlear implant; and
   transmitting, by the fitting subsystem, the fitting data generated during the fitting of the second cochlear implant to a second sound processor associated with the second cochlear implant after the fitting of the second cochlear implant to the cochlear implant patient is completed.

2. The method of claim 1, further comprising selectively communicating, by the fitting subsystem, with the first cochlear implant and the second cochlear implant by way of the first sound processor and a single clinician's programming interface ("CPI").

3. The method of claim 2, wherein the using the first sound processor to selectively fit the first cochlear implant to the cochlear implant patient comprises using the first sound processor to perform one or more fitting operations associated with the first cochlear implant while the fitting subsystem is communicatively coupled to the first cochlear implant by way of the first sound processor and the single CPI.

4. The method of claim 3, wherein the using the first sound processor to selectively fit the second cochlear implant to the cochlear implant patient comprises using the first sound processor to perform one or more fitting operations associated with the second cochlear implant while the fitting subsystem is communicatively coupled to the second cochlear implant by way of the first sound processor and the single CPI.

5. The method of claim 2, further comprising:
   detecting, by the fitting subsystem, when the fitting subsystem is communicatively coupled to the first cochlear implant; and
   detecting, by the fitting subsystem, when the fitting subsystem is communicatively coupled to the second cochlear implant.

6. The method of claim 5, wherein:
   the detecting when the fitting subsystem is communicatively coupled to the first cochlear implant comprises detecting a first unique identifier associated with the first cochlear implant; and
   the detecting when the fitting subsystem is communicatively coupled to the second cochlear implant comprises detecting a second unique identifier associated with the second cochlear implant.

7. The method of claim 6, wherein the first unique identifier comprises a first unique serial number associated with the first cochlear implant and the second unique identifier comprises a second unique serial number associated with the second cochlear implant.

8. The method of claim 6, further comprising:
maintaining, by the fitting subsystem, a first data set associated with the first unique identifier and a second data set associated with the second unique identifier;
dynamically using, by the fitting subsystem, the first data set to selectively fit the first cochlear implant to the cochlear implant patient in response to the detecting of the first unique identifier; and
dynamically using, by the fitting subsystem, the second data set to selectively fit the second cochlear implant to the cochlear implant patient in response to the detecting of the second unique identifier.

9. The method of claim 8, further comprising:
dynamically storing, by the fitting subsystem, the fitting data generated during the fitting of the first cochlear implant within the first data set; and
dynamically storing, by the fitting subsystem, the fitting data generated during the fitting of the second cochlear implant within the second data set.

10. The method of claim 8, wherein:
the first data set comprises at least one of visit history data associated with the first cochlear implant, measurement data associated with the first cochlear implant, control parameter data associated with the first cochlear implant, and diagnostic data associated with the first cochlear implant; and
the second data set comprises at least one of visit history data associated with the second cochlear implant, measurement data associated with the second cochlear implant, control parameter data associated with the second cochlear implant, and diagnostic data associated with the second cochlear implant.

11. The method of claim 1, further comprising providing, by the fitting subsystem, a first graphical user interface configured to facilitate interaction by a user with the first cochlear implant and a second graphical user interface configured to facilitate interaction by the user with the second cochlear implant.

12. The method of claim 11, wherein the providing comprises:
automatically enabling the first graphical user interface and disabling the second graphical user interface during the fitting of the first cochlear implant; and
automatically enabling the second graphical user interface and disabling the first graphical user interface during the fitting of the second cochlear implant.

13. The method of claim 1, embodied as computer-executable instructions on at least one non-transitory computer-readable medium.

14. A method comprising:
maintaining, by a fitting subsystem, a first data set associated with a first cochlear implant implanted in a patient and a second data set associated with a second cochlear implant implanted in the patient;
using, by the fitting subsystem, a first sound processor to communicatively couple the fitting subsystem to the first cochlear implant;
using, by the fitting subsystem, the first sound processor to fit the first cochlear implant to the patient in accordance with the first data set while the fitting subsystem is communicatively coupled to the first cochlear implant;
using, by the fitting subsystem, the first sound processor to communicatively couple the fitting subsystem to the second cochlear implant after a communicative decoupling of the fitting subsystem from the first cochlear implant; and
using, by the fitting subsystem, the first sound processor to fit the second cochlear implant to the patient in accordance with the second data set while the fitting subsystem is communicatively coupled to the second cochlear implant.

15. The method of claim 14, further comprising:
automatically segregating, by the fitting subsystem, fitting data generated during the fitting of the first cochlear implant from fitting data generated during the fitting of the second cochlear implant; and
transmitting, by the fitting subsystem, the fitting data generated during the fitting of the second cochlear implant to a second sound processor associated with the second cochlear implant after the fitting of the second cochlear implant is complete.

16. The method of claim 14, further comprising providing, by the fitting subsystem, a first graphical user interface configured to facilitate interaction by a user with the first cochlear implant and a second graphical user interface configured to facilitate interaction by the user with the second cochlear implant.

17. The method of claim 16, wherein the providing comprises:
automatically enabling the first graphical user interface and disabling the second graphical user interface during the fitting of the first cochlear implant; and
automatically enabling the second graphical user interface and disabling the first graphical user interface during the fitting of the second cochlear implant.

18. A system comprising:
at least one computing device that comprises
a fitting facility configured to use a first sound processor separate from the at least one computing device and associated with a first cochlear implant to selectively fit the first cochlear implant and a second cochlear implant to a cochlear implant patient; and
a data management facility communicatively coupled to the fitting facility and configured to automatically segregate fitting data generated during the fitting of the first cochlear implant from fitting data generated during the fitting of the second cochlear implant and transmit the fitting data generated during the fitting of the second cochlear implant to a second sound processor associated with the second cochlear implant after the fitting of the second cochlear implant is completed.

19. The system of claim 18, wherein the at least one computing device further comprises a communication facility configured to selectively and communicatively couple to the first cochlear implant and the second cochlear implant by way of the first sound processor.

20. The system of claim 18, wherein the at least one computing device further comprises a user interface facility configured to provide a first graphical user interface configured to facilitate interaction by a user with the first cochlear implant and a second graphical user interface configured to facilitate interaction by the user with the second cochlear implant.

* * * * *